United States Patent [19]

Sims

[11] Patent Number: 5,990,370
[45] Date of Patent: Nov. 23, 1999

[54] STEAM CRACKING OF ETHANE-RICH AND PROPANE-RICH STREAMS

[75] Inventor: David William Sims, Dunfermline, United Kingdom

[73] Assignee: BP Chemicals Limited, London, United Kingdom

[21] Appl. No.: 09/148,309

[22] Filed: Sep. 4, 1998

[30] Foreign Application Priority Data

Sep. 24, 1997 [GB] United Kingdom .................. 9720334

[51] Int. Cl.$^6$ ...................................................... C07C 4/02
[52] U.S. Cl. ........................... 585/650; 585/648; 585/302
[58] Field of Search ................................... 585/300, 302, 585/324, 648, 650

[56] References Cited

U.S. PATENT DOCUMENTS

| | | | |
|---|---|---|---|
| 3,959,401 | 5/1976 | Albright et al. | 260/683 R |
| 4,458,096 | 7/1984 | Phillips et al. | 585/302 |
| 4,492,624 | 1/1985 | Johnson et al. | 208/78 |
| 5,658,452 | 8/1997 | Heyse et al. | 208/48 R |

FOREIGN PATENT DOCUMENTS 2 231 057  7/1990  United Kingdom .

OTHER PUBLICATIONS

G. D. Hobson, Modern Petroleum Technology, Steam Cracking, pp. 453–451, Jun. 1973.

*Primary Examiner*—Hein Tran
*Attorney, Agent, or Firm*—Nixon & Vanderhye

[57] ABSTRACT

This invention relates to a process for cracking hydrocarbon feedstock comprising a mixture of ethane and propane by (a) subjecting the feedstock to a fractionation process so as to separate the feedstock into an ethane rich stream and a propane rich stream, (b) steam cracking each of these streams separately under optimum cracking conditions for each stream in separate furnaces, (c) recovering the ethylene so formed in said crackers and (d) recycling the residual uncracked ethane and propane from the cracked products to the respective ethane rich and propane rich feedstreams being fed to the steam cracker. The process enables yields of ethylene to be increased.

8 Claims, 1 Drawing Sheet

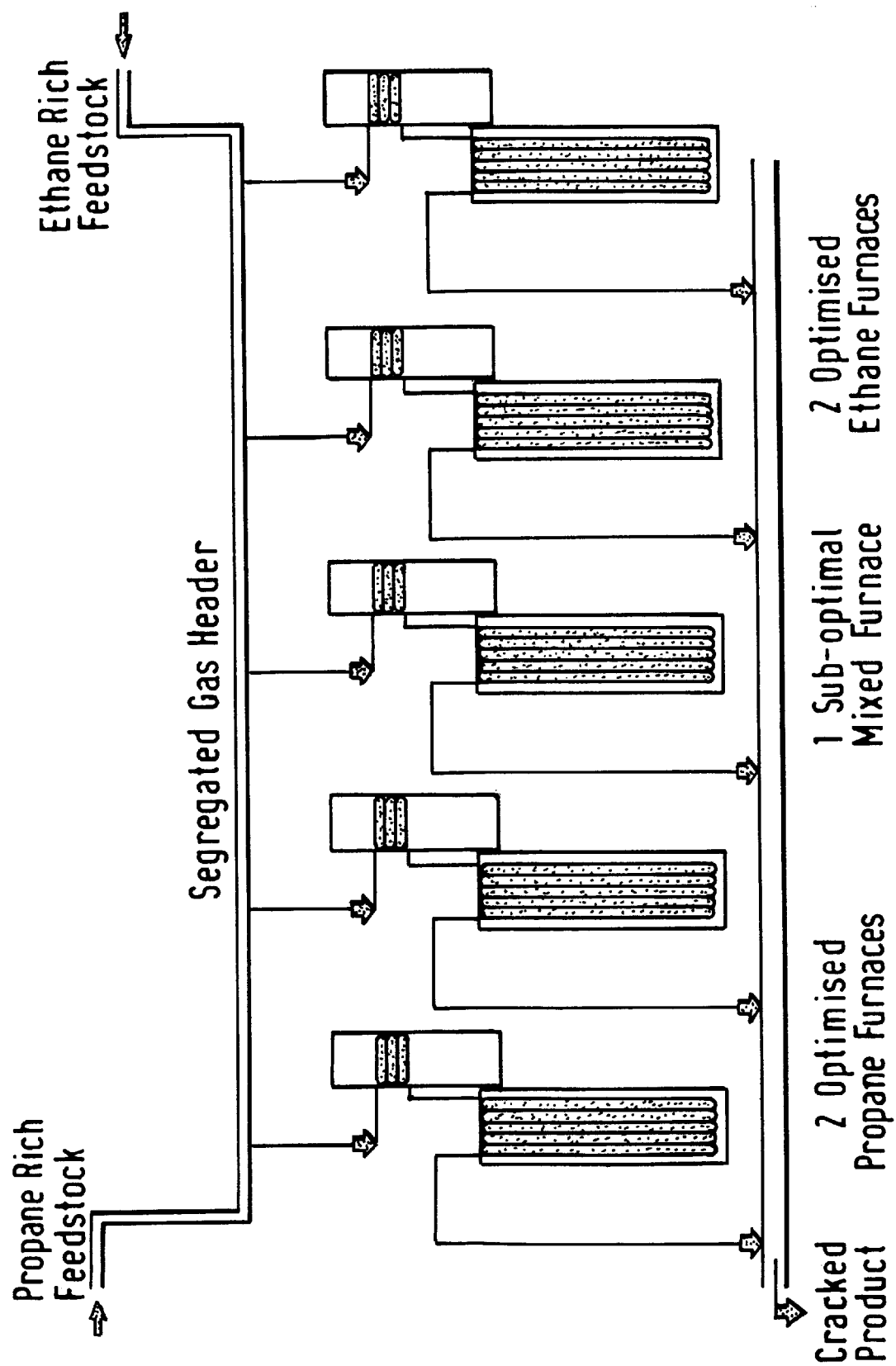

STEAM CRACKING OF ETHANE-RICH AND PROPANE-RICH STREAMS

This invention relates to a process for improving the performance of steam cracking process for producing olefins from hydrocarbon feedstocks, especially ethylene from a feedstock comprising ethane and propane.

BACKGROUND OF THE INVENTION

Methods of cracking saturated hydrocarbon feedstocks including naphthenes are well known. One of the sources of the feedstock for this steam cracking process is from a crude oil distillate. Generally, the crude oil distillate is fractionated and the lower boiling components are compressed initially and then de-compressed when a gaseous fraction comprising predominantly C1–C4 saturated hydrocarbons is released. These gases are then usually separated into a fraction comprising C1–C3 hydrocarbons predominating in ethane and propane with significant amounts of methane, and C4 hydrocarbons comprising predominantly butanes. The C1–C3 fraction is fed directly to a steam cracker in order to generate valuable ethylene and small amounts of propylene. This was usually done in the belief that normally, when cracking mixtures of paraffinic hydrocarbons, the conversion of the easier to crack component in the mixture is suppressed and the conversion of the harder to crack component is enhanced. Furthermore, the amount of ethane (sourced usually from 'dry gas', fresh ethane and recycled ethane) in such feedstock is variable due to the difficulty in storing the same when compared with the availability of propane which can be readily stored (sourced usually from LPG), and since it is not feasible to shut down a bank of crackers when the ethane availability is low. Therefore, ethane and propane have always been cracked as a mixed feedstock.

Recent studies have shown that contrary to the conventionally understood 'rules', the presence of propane in a mixed feedstock comprising propane and ethane significantly suppresses the cracking of ethane in such mixed feedstock thereby not only reducing the amount of ethylene formed in the process but also increasing the amount of ethane which has to be recycled in the process.

DESCRIPTION OF THE INVENTION

It has now been found that the yields of the ethylene from a given feedstock comprising a mixture of ethane and propane can be significantly improved by initially separating the ethane and propane and cracking them separately without adversely affecting the crackability of propane in the absence of ethane.

Accordingly, the present invention is a process for cracking hydrocarbon feedstock comprising a mixture of ethane and propane, said process comprising:
a. subjecting the feedstock to a fractionation process so as to separate the feedstock into an ethane rich stream and a propane rich stream,
b. steam cracking each of these streams separately under optimum cracking conditions for each stream in separate furnaces,
c. recovering the ethylene so formed in said crackers and
d. recycling the residual uncracked ethane and propane from the cracked products
to the respective ethane rich and propane rich feedstreams being fed to the steam cracker.

The hydrocarbon feedstock comprising ethane and propane may comprise in addition methane, n-butanes and isobutane. The separation of this mixture into ethane rich and propane rich streams can be carried out by fractionation techniques well known in the art. Each stream may contain in addition to the predominating amount of ethane and propane respectively minor amounts of the other C1–C4 components. Each of these streams comprise at least 50% v/v, preferably >60 % v/v of the respective ethane and propane and more preferably >70% v/v in the appropriate rich streams although by the very nature of the fractionation process, the ethane rich stream contains a higher proportion of methane than the propane rich stream and the latter usually contains more of the C4 hydrocarbons than the ethane rich stream.

In the steam cracking process, the relative amounts of steam to the hydrocarbon will vary with the number of carbon atoms in the feedstock to be cracked, the higher the number of carbon atoms, the more steam being used. However, for feedstock of the nature described herein, the weight ratio of steam to hydrocarbons is suitably in the range from 0.2 to 0.4, preferably from 0.25 to 0.35.

The feed rate will depend upon the cracking temperature and the type of reactor used and usually it is expressed in terms of contact time. Thus, the hydrocarbon residence time irrespective of the nature of the reactor is suitably in the range from 0.5 to 2.25 seconds, preferably from 0.5 to 1 second. For the Kinneil Gas cracker (hereafter "KG cracker" which is used in a BP Chemicals Ltd plant at Grangemouth, Scotland, UK to produce 350,000 metric tonnes per year of ethylene from a feed combination of fresh propane feedstock and Kinneil dry gas feedstock, produces ethylene of 99.95% purity and propylene of 99.6% purity) the residence time is about 1 second whereas for an older horizontal gas/oil version 4 (HGO4) cracker, the residence time is suitably about 2 seconds.

The steam cracking is suitably carried out at an inlet pressure in the range from 2–3 barg and an outlet pressure of about 0.25–0.75 barg.

The steam cracking temperature in each furnace is about from about 785–840° C.±10° C. Within this range, it is about 840° C.±10° C., especially for a KG type furnace whereas this temperature is slightly lower eg from 795–830° C. (1470–1520° F.) if an HGO4 furnace is employed.

BRIEF DESCRIPTION OF THE DRAWING

The present invention will now be described in more detail with reference to the accompanied drawing which illustrates a plurality of furnaces.

One of the features of the present invention is that the process can be designed with minimal expense to steam crack ethane rich and propane rich streams separately, in spite of the uncertainty of ethane supplies without shutting down any of the crackers. This is achieved by having a plurality of furnaces, say, eg a bank of five (5) furnaces or crackers arranged in series 1–5, and feeding the mainly propane rich streams into crackers 1 and 2 at one end and the ethane rich stream into furnaces 4 and 5 at the opposite end. The one is the middle (furnace 3) can be used to crack a mixed feed of ethane and propane or either of these hydrocarbons separately depending upon their availability. The products from each of these furnaces is withdrawn from the base of the respective furnaces and the ethylene in the products from each of the five furnaces is recovered and the unreacted/uncracked materials in each of the remaining streams then pooled together for recycle to the appropriate feed streams for each of said furnaces.

The process of the present invention enables conversion of ethane to be increased well above 60% and propane conversions in excess of 90% have been achieved.

In a typical process, gas feedstock comprising ethane and propane flow to the hydrocarbon pre-heat bank via flow control valves provided on each furnace. Each line divides into three passes resulting in a six pass pre-heat bank. The feed leaves this bank at a temperature ranging from 329–336° C. depending upon the feedstock and furnace fouling. At each end of the furnace the three passes recombine into a single line. Dilution steam is treated with dimethyl disulphide (DMDS) which acts as a passivating agent on the nickel of the radiant coils, to minimise coke/CO formation. The combined hydrocarbon/steam mixture splits into a plurality of passes before entering the hydrocarbon/steam pre-heat bank. In this bank, the gases are heated to a temperature which is close to the initial cracking temperature, but sufficiently below to prevent coke formation. The process temperature at this point varies from 626–671° C.

The six hydrocarbon/steam passes enter two mixing fittings. Each mixing fitting supplies feed to a plurality of radiant coils. Flow distribution is via venturi nozzles operating at critical flow. In this regime, the flow is independent of the pressure downstream of the nozzle. This design ensures equal flow distribution to each coil regardless of the relative coil fouling. As long as the pressure ratio (Pout/Pin) is below 0.85, critical flow will be maintained and coil coking will be relatively uniform.

The hydrocarbon/steam mixture is rapidly heated in the cracking coils in a radiant box. Each vertically-mounted coil has a plurality of legs with return bends at both top and bottom. The coils are fabricated from material which is capable of tolerating the extreme temperature that exists in a firebox used in such crackers. Each coil enters and exits the firebox through the roof. Cracking occurs primarily eg in the last three legs of eg a six-legged coil. The coil is swagged to a larger diameter after three legs to minimise the pressure drop due to coke deposition and the increased volumetric flow caused by pressure, temperature and molecular expansion. The coil outlet temperature varies from 823–838° C.

The cracked gas from each radiant coil flows through a short transfer line into a heat exchanger. The cracking reaction is quickly quenched to a temperature between 576 and 592° C., the quenched products then entering large diameter collection headers. The cracked gaseous products from the collection headers are manifolded into a single line feeding a further heat exchanger where these gases are cooled further to a temperature of about 350–400° C. and are taken off. The reaction products are separated by compression and fractional distillation techniques known in the art.

EXAMPLES

The present invention is illustrated with reference to the following Examples and Comparative Tests (not according to the invention). Each of these Examples and Tests were carried out by a process illustrated in the accompanying flow diagram. In the diagram, propane and dry gas were supplied to the KG cracker from the Kinneil plant, the propane being stored on plot in two 200 tonne bullets. Normal-butane was stored in a 200 tonne bullet on the KG cracker plot.

Gas feedstock flowed to the hydrocarbon pre-heat bank via two flow control valves (not shown) per furnace. Dilution steam was treated with DMDS before combining on flow control with the two hydrocarbon lines. The hydrocarbon-steam mixtures were rapidly heated in the cracking coils in a radiant box. The steam ratio in the C2/C3 hydrocarbon mixtures cracking trials were at about 0.30 and in the case of C3/C4 hydrocarbon mixtures, the steam ratio was set proportional to the feed mix, ie 0.30 for dedicated propane tending towards 0.40 for field butanes. However, for a given feed mix, the ratio was maintained essentially constant. The cracking was carried out primarily in the last three passes of a six-pass coil. The coil outlet temperature varied from about 823–832° C., unless otherwise indicated, depending upon feedstock. The cracked gas from each radiant coil flowed through a short transfer line into a USX Exchanger.

In the Tables below, the following abbreviations have been used:

S/H—Steam/Hydrocarbon weight ratio

CIP—Coil inlet pressure

CIT—Coil inlet temperature

CEP—Coil exit pressure

CET—Coil exit temperature

C3 acet.—C3 acetylenes including methyl acetylene and propadiene.

The results in Tables 1 to 3 are self-explanatory and show the conventional methods used. Table 4 shows that when using the same average feed composition, two furnaces operating with the feed composition of Run No. 2 plus one furnace operating with the feed composition of Run No. 3 produce more ethylene than three furnaces operating with the feed composition of Run No. 1.

In Table 5, shows the product distribution for a mixed feed (Case 1), ethane/dry gas feed (Case 2) and propane feed (Case 3) at the same furnace operating conditions. Case 4 is a weighted average of Cases 2 and 3 plus some extra methane to give the same overall feed composition as Case 1. The "change in yield" column shows the difference between Case 4 and Case 1, a reduction in ethane content by 3.8% by weight, an increase in ethylene content by 1.8% by weight and an increase in methane content by 1.5% by weight.

TABLE 1

KG Dedicated Propane Cracking Yields

| Pure Propane Conversion (%) | 84 | 86 | 88 | 90 | 92 |
|---|---|---|---|---|---|
| | | | YIELDS | | |
| Hydrogen | 1.50 | 1.54 | 1.59 | 1.63 | 1.67 |
| Methane | 20.72 | 21.67 | 22.61 | 23.55 | 24.49 |
| Ethane | 3.03 | 3.14 | 3.25 | 3.36 | 3.46 |
| Ethylene | 32.35 | 33.72 | 34.88 | 36.04 | 37.19 |
| Acetylene | 0.15 | 0.32 | 0.49 | 0.66 | 0.82 |
| Propane | 16.00 | 14.00 | 12.00 | 10.00 | 8.00 |
| Propylene | 16.34 | 15.65 | 14.97 | 14.29 | 13.61 |
| C3 acet. | 0.33 | 0.35 | 0.37 | 0.39 | 0.41 |
| Butadiene | 1.94 | 2.07 | 2.19 | 2.31 | 2.43 |
| Iso-butene | 0.05 | 0.05 | 0.05 | 0.05 | 0.05 |
| n-Butane | 0.04 | 0.04 | 0.03 | 0.03 | 0.02 |
| Iso-Butane | 0.08 | 0.06 | 0.05 | 0.04 | 0.03 |
| Butene-1 | 1.04 | 0.96 | 0.89 | 0.82 | 0.75 |
| Butene-2 | 0.44 | 0.45 | 0.45 | 0.46 | 0.46 |
| Benzene | 1.61 | 1.74 | 1.86 | 1.98 | 2.10 |
| Other gasoline | 3.08 | 3.17 | 3.25 | 3.33 | 3.41 |
| Fuel oil | 1.10 | 1.10 | 1.10 | 1.10 | 1.10 |

TABLE 2

KG Dedicated Ethane Cracking Yields
(Based on Extrapolated Model Data)

| Pure Ethane Conversion (%) | 50 | 55 | 60 | 65 |
|---|---|---|---|---|
| | | YIELDS | | |
| Hydrogen | 2.66 | 2.92 | 3.19 | 3.45 |
| Methane | 4.23 | 4.30 | 4.37 | 4.44 |
| Ethane | 50.00 | 45.00 | 40.00 | 35.00 |
| Ethylene | 43.38 | 45.72 | 48.06 | 50.40 |
| Acetylene | 0.30 | 0.33 | 0.36 | 0.38 |
| Propane | 0.00 | 0.00 | 0.00 | 0.00 |
| Propylene | 0.31 | 0.21 | 0.10 | 0.01 |
| C3 acet. | −0.01 | 0.00 | 0.01 | 0.02 |
| Butadiene | 0.65 | 0.86 | 1.07 | 1.27 |
| Iso-butene | 0.02 | 0.04 | 0.07 | 0.09 |
| n-Butane | 0.12 | 0.13 | 0.13 | 0.13 |
| Iso-Butane | −0.04 | 0.00 | 0.04 | 0.08 |
| Butene-1 | 0.00 | 0.00 | 0.00 | 0.00 |
| Butene-2 | 0.00 | 0.00 | 0.00 | 0.00 |
| Benzene | −0.74 | 0.25 | 1.24 | 2.23 |
| Other gasoline | −1.01 | 0.09 | 1.20 | 2.31 |
| Fuel oil | 0.14 | 0.16 | 0.17 | 0.19 |

TABLE 3

(Not according to the invention)
KG C2/C3 Furnace: Typical Yield Patterns at 28 te/hr

| Severity | High | Low | High | Low | High | Low | High | Low |
|---|---|---|---|---|---|---|---|---|
| | | | Propane in Feed Mix (%) | | | | | |
| Temp. (° C.) | 843 | 838 | 843 | 838 | 843 | 838 | 842 | 838 |
| $C_2H_6$ Conv. % | 60.0 | 57.5 | 56.0 | 54.0 | 52.0 | 50.0 | — | — |
| $C_3H_8$ Conv. % | 92.0 | 90.0 | 91.0 | 89.0 | 90.0 | 88.0 | 89.0 | 87.0 |
| Feed | | | Composition by mass fraction | | | | | |
| Methane | 0.07 | 0.07 | 0.04 | 0.04 | 0.02 | 0.02 | 0.00 | 0.00 |
| Ethane | 0.53 | 0.53 | 0.46 | 0.46 | 0.38 | 0.38 | 0.00 | 0.00 |
| Propane | 0.40 | 0.40 | 0.50 | 0.50 | 0.60 | 0.60 | 1.00 | 1.00 |
| | | | | YIELDS | | | | |
| Hydrogen | 2.36 | 2.27 | 2.19 | 2.12 | 2.03 | 1.96 | 1.61 | 1.56 |
| Methane | 19.11 | 18.72 | 18.00 | 17.51 | 17.75 | 17.17 | 23.08 | 22.14 |
| Ethane | 22.59 | 23.87 | 21.95 | 22.81 | 20.25 | 20.95 | 3.30 | 3.20 |
| Ethylene | 40.35 | 39.26 | 39.54 | 38.53 | 38.44 | 37.39 | 35.44 | 34.28 |
| Acetylene | 0.52 | 0.44 | 0.52 | 0.43 | 0.51 | 0.41 | 0.57 | 0.41 |
| Propane | 3.20 | 4.00 | 4.50 | 5.50 | 6.00 | 7.20 | 11.00 | 13.00 |
| Propylene | 5.49 | 5.80 | 7.06 | 7.42 | 8.68 | 9.10 | 14.63 | 15.31 |
| C3 Acet. | 0.17 | 0.16 | 0.20 | 0.19 | 0.23 | 0.22 | 0.38 | 0.36 |
| Butadiene | 1.54 | 1.44 | 1.60 | 1.50 | 1.67 | 1.56 | 2.25 | 2.13 |
| Iso-butene | 0.06 | 0.05 | 0.05 | 0.04 | 0.04 | 0.04 | 0.05 | 0.05 |
| n-Butane | 0.08 | 0.08 | 0.07 | 0.07 | 0.06 | 0.06 | 0.03 | 0.03 |
| Iso-butane | 0.03 | 0.03 | 0.02 | 0.02 | 0.01 | 0.02 | 0.04 | 0.06 |
| Butene-1 | 0.30 | 0.33 | 0.39 | 0.43 | 0.49 | 0.53 | 0.85 | 0.93 |
| Butene-2 | 0.18 | 0.18 | 0.23 | 0.23 | 0.27 | 0.27 | 0.45 | 0.45 |
| Benzene | 1.50 | 1.19 | 1.23 | 0.99 | 1.06 | 0.84 | 1.92 | 1.80 |
| Other Gasoline | 2.00 | 1.68 | 1.83 | 1.59 | 1.78 | 1.56 | 3.29 | 3.21 |
| Fuel Oil | 0.53 | 0.53 | 0.62 | 0.62 | 0.72 | 0.71 | 1.10 | 1.10 |

TABLE 4

Results from conventional KG cracker using mixed C2/C3 feeds
(The results have been converted to methane-free feed basis)

| | Run No. | | |
|---|---|---|---|
| Feed (% wt/wt) | 1* | 2 | 3 |
| Ethane | 38.37 | 57.55 | 0.24 |
| Ethylene | 0.00 | 0.09 | 0.00 |
| Propane | 60.19 | 41.63 | 98.26 |
| Propylene | 0.31 | 0.36 | 1.12 |
| C4's | 1.13 | 0.38 | 0.38 |
| | Product (% wt/wt) | | |
| Hydrogen | 2.08 | 2.55 | 1.67 |
| Methane | 16.98 | 12.70 | 24.30 |
| Ethane | 19.37 | 25.00 | 3.23 |
| Ethylene | 39.98 | 43.36 | 36.89 |
| Acetylene | 0.54 | 0.53 | 0.64 |
| Propane | 5.38 | 3.45 | 9.55 |
| Propylene | 8.15 | 5.59 | 13.82 |
| C3 Acet. | 0.23 | 0.16 | 0.38 |
| Iso-butane | 0.05 | 0.07 | 0.03 |
| n-Butane | 0.08 | 0.10 | 0.02 |
| Butene-1 | 0.35 | 0.27 | 0.71 |
| Iso-butene | 0.10 | 0.05 | 0.12 |
| Butene-2 | 0.24 | 0.18 | 0.46 |
| Butadiene | 1.72 | 1.62 | 2.37 |
| Benzene | 1.67 | 1.61 | 1.69 |
| Toluene | 0.25 | 0.21 | 0.26 |
| Others | 2.81 | 2.52 | 3.85 |
| | Conversion | | |
| Ethane | 53.5 | 58.2 | — |
| Propane | 91.1 | 91.7 | 90.3 |

*Not according to the invention

TABLE 5

Evaluation of change in product yields using a split feed header to feed ethane and propane separately into different crackers

| | Mixed Feed | Split Feed Header | | | |
|---|---|---|---|---|---|
| | Case 1 | Case 2 | Case 3 | Case 4 | Yield* |
| Flow Rate | 23.1 | 22.3 | 22.9 | | |
| S/H | 0.30 | 0.30 | 0.30 | | |
| CIP (barg.) | 1.53 | 1.69 | 1.68 | | |
| CIT (° C.) | 648 | 671 | 651 | | |
| CEP (barg.) | 0.54 | 0.64 | 0.53 | | |
| CET (° C.) | 831.4 | 830.5 | 832.2 | | |
| Feed | | Concentration (% wt/wt) | | | |
| Methane | 5.77 | 9.70 | 0.05 | 5.77 | 0.00 |
| Ethane | 34.79 | 66.51 | 0.42 | 34.78 | −0.01 |
| Ethylene | 0.12 | 0.00 | 0.00 | 0.00 | −0.19 |
| Propane | 58.39 | 23.40 | 97.42 | 58.25 | −0.13 |
| Propylene | 0.28 | 0.23 | 1.47 | 0.81 | +0.53 |
| Iso-butane | 0.55 | 0.14 | 0.59 | 0.35 | −0.20 |
| n-Butane | 0.10 | 0.04 | 0.05 | 0.04 | −0.06 |
| | | | YIELDS | | |
| Hydrogen | 1.99 | 2.85 | 1.45 | 2.16 | +0.17 |
| Methane | 20.44 | 20.30 | 22.67 | 21.98 | +1.54 |
| Ethane | 17.26 | 22.92 | 3.28 | 13.47 | −3.79 |
| Ethylene | 37.63 | 44.86 | 34.01 | 39.41 | +1.78 |
| Acetylene | 0.59 | 0.57 | 0.55 | 0.56 | −0.03 |
| Propane | 6.91 | 1.44 | 11.99 | 6.41 | −0.50 |
| Propylene | 9.27 | 2.98 | 15.55 | 8.91 | −0.35 |
| C3 Acet. | 0.21 | 0.08 | 0.36 | 0.21 | 0 |
| Iso-butane | 0.02 | 0.00 | 0.05 | 0.02 | 0 |
| n-Butane | 0.04 | 0.11 | 0.02 | 0.06 | +0.02 |
| Butene-1 | 0.36 | 0.16 | 0.55 | 0.35 | −0.01 |
| Iso-butene | 0.10 | 0.00 | 0.52 | 0.25 | +0.15 |
| Butene-2 | 0.24 | 0.15 | 0.43 | 0.28 | +0.04 |
| Butadiene | 1.69 | 1.53 | 2.14 | 1.81 | +0.12 |
| Gasoline + Fuel Oil | 3.28 | 2.06 | 6.42 | 4.11 | +0.83 |

*Change in yield (Case 4 minus Case 1)

The process of the present invention is capable of improving the conversion of ethane significantly when the ethane rich stream is cracked separately from the propane rich stream and consequently improves the yield of ethylene from the same amount of ethane and propane by about 1.78% by weight or 4.73% (relative). This represents a considerable improvement in the economics of the process.

I claim:

1. A process for cracking hydrocarbon feedstock comprising a mixture of ethane and propane, said process comprising:
   a. subjecting the feedstock to a fractionation process so as to separate the feedstock into a first stream which comprises more than 50% v/v ethane and a second stream which comprises more than 50% v/v propane,
   b. steam cracking each of these streams separately under optimum cracking conditions for each stream in separate crackers,
   c. recovering the ethylene so formed in said crackers and
   d. recycling residual uncracked ethane and propane from cracked products to the respective first and second streams being fed to the steam cracker.

2. A process according to claim 1 wherein the hydrocarbon feedstock comprising ethane and propane further comprises methane, C4 hydrocarbons (n-butanes and isobutane).

3. A process according to claim 2 wherein the fractionation is carried out such that the first stream contains a higher proportion of methane than the second stream and the second stream contains more C4 hydrocarbons than the first stream.

4. A process according to claim 1 wherein during the steam cracking, the weight ratio of steam to hydrocarbon is in the range from 0.2 to 0.4.

5. A process according to claim 1 wherein the feed rate is such that the residence time of the hydrocarbon and steam is in the range from 0.5 to 2.25 seconds.

6. A process according to claim 1 wherein the steam cracking is carried out at an inlet pressure in the range from 2–3 barg and an outlet pressure of about 0.25–0.75 barg.

7. A process according to claim 1 wherein the steam cracking temperature in each cracker is from about 785–840° C.±10° C.

8. A process according to claim 1 wherein the separate cracking is achieved by having a plurality of crackers arranged in series and feeding the second stream into the first two crackers at one end and the first stream into the last two crackers at the opposite end, the ones in the middle being used to crack a mixed feed of ethane and propane or either of these hydrocarbons separately, whereby the products from each of these crackers is withdrawn from the base thereof and the ethylene in the products from each of the crackers is recovered, the unreacted/uncracked materials in each of the remaining streams being pooled together for recycle to the appropriate feed streams to said crackers.

* * * * *